(12) United States Patent
Maierhofer (10) Patent No.: US 12,324,875 B2
(45) Date of Patent: *Jun. 10, 2025

(54) METHOD AND DEVICES FOR DETERMINING A TREATMENT REGIMEN FOR ALTERING THE TREATMENT PARAMETERS WHEN DIALYZING A PATIENT

(71) Applicant: Fresenius Medical Care Deutschland GmbH, Bad Homburg (DE)

(72) Inventor: Andreas Maierhofer, Schweinfurt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 2 days.

This patent is subject to a terminal disclaimer.

(21) Appl. No.: 18/462,881

(22) Filed: Sep. 7, 2023

(65) Prior Publication Data

US 2023/0414848 A1   Dec. 28, 2023

Related U.S. Application Data

(63) Continuation of application No. 16/956,281, filed as application No. PCT/EP2018/085222 on Dec. 17, 2018, now Pat. No. 11,786,644.

(30) Foreign Application Priority Data

Dec. 19, 2017   (DE) .......................... 102017130548.3

(51) Int. Cl.
*A61M 1/16*   (2006.01)
*A61M 1/34*   (2006.01)
(Continued)

(52) U.S. Cl.
CPC ........ *A61M 1/1611* (2014.02); *A61M 1/1605* (2014.02); *A61M 1/1613* (2014.02);
(Continued)

(58) Field of Classification Search
CPC .......................... A61M 1/1611; A61M 1/1605; A61M 1/1613; A61M 1/1656; A61M 1/341;
(Continued)

(56) References Cited

U.S. PATENT DOCUMENTS

| | | |
|---|---|---|
| 8,764,987 B2 | 7/2014 | Gross et al. |
| 10,349,876 B2 | 7/2019 | Maierhofer |

(Continued)

FOREIGN PATENT DOCUMENTS

| | | |
|---|---|---|
| EP | 2413991 | 5/2018 |
| EP | 3183013 | 10/2019 |

(Continued)

OTHER PUBLICATIONS

D. Daniel E. Weiner, et al., "Improving Clinical Outcomes Among Hemodialysis Patients: A Proposal for a "Volume First" Approach From the Chief Medical Officers of US Dialysis Providers", American Journal of Kidney Diseases, vol. 64, Issue 5, 2014, pp. 685-695. (Year: 2014).*

(Continued)

*Primary Examiner* — Amber A Misiaszek
(74) *Attorney, Agent, or Firm* — Fish & Richardson P.C.

(57) ABSTRACT

A method for determining a treatment regimen for altering the treatment parameters when dialyzing a patient over a plurality of treatment sessions taking place on future days includes determining a diffusive total target sodium balance; and determining a transitional treatment regimen by which the diffusive total target sodium balance is achieved over the plurality of future treatment sessions. A control device or closed-loop control device is configured to control a blood treatment apparatus using the method.

16 Claims, 3 Drawing Sheets

(51) Int. Cl.
| | |
|---|---|
| *G05B 6/02* | (2006.01) |
| *G16H 20/40* | (2018.01) |
| *G16H 40/40* | (2018.01) |
| *G16H 40/63* | (2018.01) |
| *G16H 50/20* | (2018.01) |
| *G16H 50/30* | (2018.01) |
| *G16H 50/50* | (2018.01) |

(52) U.S. Cl.
CPC .......... *A61M 1/1656* (2013.01); *A61M 1/341* (2014.02); *G05B 6/02* (2013.01); *G16H 20/40* (2018.01); *G16H 40/40* (2018.01); *G16H 40/63* (2018.01); *G16H 50/20* (2018.01); *G16H 50/30* (2018.01); *G16H 50/50* (2018.01)

(58) Field of Classification Search
CPC ..... A61M 1/1601; A61M 1/1654; G05B 6/02; G16H 20/40; G16H 40/40; G16H 40/63; G16H 50/20; G16H 50/30; G16H 50/50
See application file for complete search history.

(56) References Cited

U.S. PATENT DOCUMENTS

| | | | |
|---|---|---|---|
| 2006/0122540 A1* | 6/2006 | Zhu ...................... | A61B 5/0537 600/587 |
| 2006/0226079 A1* | 10/2006 | Mori ...................... | A61M 1/16 210/85 |
| 2013/0172806 A1 | 7/2013 | Griessmann et al. | |
| 2013/0274644 A1 | 10/2013 | Hertz | |
| 2014/0067416 A1 | 3/2014 | Duelsner et al. | |
| 2014/0158623 A1* | 6/2014 | Pudil ................... | A61M 1/3472 210/96.2 |
| 2016/0022892 A1 | 1/2016 | Eifler et al. | |
| 2020/0108195 A1* | 4/2020 | Aota ...................... | A61M 1/14 |

FOREIGN PATENT DOCUMENTS

| | | |
|---|---|---|
| JP | 2012-521816 | 9/2012 |
| WO | WO 2012/038384 | 3/2012 |

OTHER PUBLICATIONS

Song et al., "Effect of Sodium Balance and the Combination of Ultrafiltration Profile during Sodium Profiling Hemodialysis on the Maintenance of the Quality of Dialysis and Sodium and Fluid Balances," Journal of the American Society of Nephrology, Jan. 2005, 16(1):237-246.

International Search Report in International Appln. No. PCT/EP2018/085222, mailed Mar. 26, 2019, 3 pages.

Keen et al., "The Association of the Sodium "Setpoint" to Interdialytic Weight Gain and Blood Pressure in Hemodialysis Patients," The International Journal of Artificial Organs, Nov. 2007, 30(11):971-979.

Raja et al., "Sequential changes in dialysate sodium (DNa) During Hemodialysis," Transactions—American Society for Artificial Internal Organs, Apr. 1983, 649-651.

Song et al, "Time-averaged concentration of dialysate sodium relates with sodium load and interdialytic weight gain during sodium-profiling hemodialysis," American Journal of Kidney diseases, Aug. 2002, 40(2): 291-301.

Weiner et al., "Improving Clinical Outcomes Among Hemodialysis Patients: A Proposal for a "Volume First" Approach From the Chief Medical Officers of US Dialysis Providers," American Journal of Kidney Diseases, Nov. 2014, 64(5):685-695.

Reißenweber, "Sodium Profiles: Utilization of Modern Technical Dialysis Machines," Dialyse aktuell, 215, 19:24-30, 14 pages (with English machine translation).

* cited by examiner

METHOD AND DEVICES FOR DETERMINING A TREATMENT REGIMEN FOR ALTERING THE TREATMENT PARAMETERS WHEN DIALYZING A PATIENT

CROSS-REFERENCE TO RELATED APPLICATIONS

This application is a continuation application of and claims the benefit of priority under 35 U.S.C. § 120 to U.S. application Ser. No. 16/956,281, filed on Jun. 19, 2020, which is the national stage entry of International Patent Application No. PCT/EP2018/085222, filed on Dec. 17, 2018, and claims priority to Application No. DE 10 2017 130 548.3, filed in the Federal Republic of Germany on Dec. 19, 2017. The disclosure of each application is incorporated herein in its entirety by reference thereto.

TECHNICAL FIELD

The present disclosure relates to a method, a control device or a closed-loop control device, and a blood treatment apparatus. Furthermore, the present disclosure relates to a digital storage medium, a computer program product, and a computer program.

BACKGROUND

During extracorporeal blood treatment, the patient's blood is taken and led along an extracorporeal blood circuit and, for example, through a blood filter. The blood filter comprises a blood chamber through which blood is led, and a dialysis liquid chamber, through which dialysis liquid is led. Both chambers are separated from each other by a semi-permeable membrane. Blood and dialysis liquid are mostly guided by the counter current principle through the blood filter. The blood is cleaned in the blood filter. On exiting the blood filter, the dialysis liquid, from now on referred to as dialysate, is regarded as used and is discarded. In addition to the dialysate, the fluid to be discarded also comprises filtrate, which comprises water which was withdrawn from the blood in the blood filter. Filtrate and dialysate will be referred to individually or collectively in the following simply as effluent. In addition to acute cases, dialysis is used particularly for patients with end-stage renal disease.

Patients with end-stage renal disease have limited or no ability to excrete toxins and liquid accumulating in the body. Therefore, these patients depend on the extracorporeal method of dialysis for regularly removing or degrading the accumulation. Hence, for most patients hemodialysis treatment is carried out typically three times a week. In addition to the removal of substances like urea and potassium, it is an essential task of the dialysis to degrade the overhydration of the patient resulting from liquid ingestion by liquid removal from the blood such that the patient ideally reaches again his dry weight after the dialysis. This condition may be determined by various clinical methods, with which the bio-impedance is currently preferred. The liquid ingestion between dialysis treatments is closely linked to the salt content of the diet as a change in sodium concentration in the blood via physiological control mechanisms controls the sensation of thirst. In doing so, the body aims at a "sodium setpoint" being dependent on the individual physiology (Keen, M. L., & Gotch, F. A., The association of the sodium "setpoint" to interdialytic weight gain and blood pressure in hemodialysis patients, The International Journal of Artificial Organs/Vol. 3/no. 11, 2007/pages 971-979). If this "setpoint" is exceeded by salt ingestion through the diet or through salt intake during dialysis, it causes a feeling of thirst. Due to the consequential liquid ingestion, the sodium concentration (short: Na-concentration) is then led back to the "setpoint". Clinical studies have shown that the mortality of dialysis patients increases with both the degree of chronic overhydration and the degree of relative interdialytic weight gain or increase caused by liquid ingestion.

SUMMARY

In the body, the water is distributed among various physiological compartments, which may be divided in the intracellular space, the extracellular space and the interstitium (Guyton & Hall, Textbook of Medical *Physiology*). The distribution among these compartments is mainly determined by the osmotic equilibrium to which the sodium content in these compartments contributes most. In hemodialysis, both a mass transfer with the blood and a liquid removal from blood take place in the dialyzer. After returning blood to the body, a new equilibrium respectively arises due to a filling flow of liquid from other parts of the body and due to a balancing of the substance concentration. These processes however need a certain amount of time, making it possible that the removal of liquid from the blood via dialysis is faster than the flow of body water. Due to the decrease of the volume (or the amount) of water in the blood vessels caused thereby, a blood pressure decrease and possibly a critical blood pressure drop may occur during the dialysis. This may be partially counteracted by increasing the salt concentration in the blood diffusive salt transfer in the dialyzer. For this purpose, the sodium concentration in the dialysis liquid is selected such that it is above the blood sodium concentration. As a result, this leads by an increase in osmolarity in the blood to an increase in the flow of body water. However, such an intradialytic salt administration concurrently leads to an increase in the salt concentration in the body and thus to increased thirst, which is compensated in during the period between the treatment sessions by an increased liquid ingestion. Because of this, however, the overhydration of the patient is increased such that in the next dialysis session a correspondingly larger volume of liquid must be removed. Therefore, such an intradialytic salt administration should be avoided if possible.

A treatment regimen, or a method for determining a treatment regimen, determines or alters one or several treatment parameters during the dialysis of a patient over a plurality of future treatment sessions, taking place on future days.

The method encompasses determining a value denoted herein as diffusive total target sodium balance, which is herein the target value of the diffusive sodium balance which should be reached as desired after a plurality of future treatment sessions in one of the future treatment sessions.

The diffusive sodium balance and its determination is as such described in e.g., EP 2 413 991 A1 and in U.S. Pat. No. 8,764,987, the relevant content of which is hereby incorporated in its entirety by reference as the subject matter also of this application.

The diffusive sodium balance may represent the transfer of mass, substance or molecules between dialysate and blood running without a reduction of blood volume. As a result of this sodium diffusion, the sodium concentration in the blood changes, which leads to physiological effects (in case of sodium increase, e.g.: circulatory stabilization, thirst; in case of sodium decrease e.g.: blood pressure drops, convulsions).

The diffusive sodium balance may be understood e.g., as a result of a mass transfer without accompanying volume reduction.

This diffusive total target sodium balance is achieved using the using the method, preferably with a first or a later treatment session planned using the method, but at least upon or after completion of the method or of the transitional treatment regimen described below.

The diffusive sodium balance, may be measured e.g., between the blood compartment and the dialysis liquid compartment of the dialyzer. Alternatively, the diffusive sodium balance, in particular with the peritoneal dialysis, may be measured by comparing the sodium content of fresh dialysis liquid delivered to the patient on the one hand, with the sodium content of the used dialysate being removed from the patient in the same treatment session, on the other hand. This measurement may reveal whether the diffusive total target sodium balance (as a target value) was already reached or not.

The method further encompasses determining a transitional treatment regimen by which during the treatment session (or over a plurality of future treatment sessions, or following these), and e.g., towards its end, the diffusive total target sodium balance is achieved.

"Reaching" as well as "achieving" the diffusive total target sodium balance" may be understood e.g., as treatment of the patient with a diffusive sodium balance which is tolerated by the patient in a treatment session.

In this, a proposal is made as to how the diffusive total target sodium balance is stepwise prepared over several treatment sessions, in that for instance the diffusive sodium balance may be reduced from a higher diffusive sodium balance, which was tolerated by the patient in the previous treatment sessions or the diffusive sodium balance to which the patient is used to a lower desired diffusive sodium balance, namely the diffusive total target sodium balance. The diffusive total target sodium balance may thus be the target of gradually lowering an original diffusive sodium balance or a diffusive initial sodium balance. In this, the diffusive sodium balance, which is respectively set on the current treatment day or achieved by treatment, may gradually approach the diffusive total target sodium balance or assume the value thereof following a plurality of treatment sessions.

Alternatively, the diffusive total target sodium balance may be already set in, or proposed for, the first treatment session. In order to make the setting tolerable for the patient, other parameters may be adapted or changed in the treatment planning relieving the patient, as explained below.

In some embodiments, an ultrafiltration function, or to a use of an ultrafiltration function, of a provided blood treatment apparatus for the dialysis of a patient, wherein the ultrafiltration volume removed or to be removed from the patient using ultrafiltration is determined by the method for specifying a treatment regimen. The ultrafiltration function may be an ultrafiltration. The ultrafiltration function may be carried out by the blood treatment apparatus which may comprise a control device or closed-loop control device, for example the control device or closed-loop control device, being configured for initiating or performing the ultrafiltration function.

In some embodiments, sodium (or sodium chloride) or a dialysis liquid, or to using sodium or sodium chloride, each incorporated into a dialysis liquid, or to using the dialysis liquid, each for the dialysis of a patient. The concentration of the sodium chloride, in particular in the dialysis liquid, is determined in order to achieve a diffusive sodium balance in one or in a plurality of treatment sessions, wherein the diffusive sodium balance to be achieved is determined using the method for determining a treatment regimen. Alternatively or additionally, it is determined by the method for determining a treatment regimen how the desired diffusive sodium balance is or should be achieved by using the sodium or the dialysis liquid.

In some embodiments, a method for mixing a dialysis liquid for the dialysis treatment of a patient, wherein the concentration of the sodium chloride is determined for one or a plurality of treatment sessions using the method for determining a treatment regimen.

A control device or a closed-loop control device is configured or programmed for executing and/or for prompting the execution of each of the methods, in particular in each embodiment described herein and in each possible combination of features disclosed herein, in particular method steps. The control device or closed-loop control device is additionally or alternatively configured or programmed to control or closed-loop control a blood treatment apparatus based on the results of the method or based on the values or parameters determined, provided, stored and/or defined hereby or herein.

The control device or closed-loop control device may comprise, or be in signal communication with devices which execute the individual method steps or method features as herein—and in particular in the claims—disclosed and which are correspondingly designed, configured and/or programmed. These devices may be named according to the step performed or performable by them.

In particular the control device or the closed-loop control device optionally comprises, or is in signal communication with, a device for determining a value, herein referred to as diffusive total target sodium balance.

In particular, the control device or the closed-loop control device further optionally comprises, or is connected in signal communication to, a device for determining a transitional treatment regimen by which the diffusive total target sodium balance is achieved during the treatment session (or over the plurality of future treatment sessions), and e.g., towards its end.

In some embodiments, a blood treatment apparatus. It optionally comprises, or is connected in signal communication to, a control device, in particular to be controlled or closed-loop controlled therewith. Additionally or alternatively, the blood treatment apparatus comprises a control device or closed-loop control device which is configured or programmed to control or closed-loop control the blood treatment apparatus based on the results of the method or based on the values or parameters determined, provided, stored and/or defined hereby or herein.

A digital, in particular non-volatile, storage medium, in particular a floppy disk, memory card, CD, DVD, Blu-ray disc or (E)EPROM, with electronically readable control signals, may interact with a programmable computer system such that the, in particular machine-induced, steps of a method are prompted.

In this, all, several or some of the, in particular machine-induced, steps of the method may be prompted.

A computer program product comprises a program code, volatile or saved on a machine-readable storage medium for prompting the machine-induced steps of the method when the computer program product runs on a computer. A computer program product can be understood as, for example, a computer program which is stored on a data storage medium, an embedded system as a comprehensive system with a computer program (for example, an electronic device with a computer program), a network of computer-implemented computer programs (for example, a client-server system, a cloud computing system, etc.) or a computer on which a computer program is loaded, running, saved, executed or developed.

The term "machine-readable storage medium", as used herein, denotes in certain exemplary embodiments a medium, which contains data or information, which is interpretable by software and/or hardware. The medium may be a data medium such as a floppy disk, a CD, DVD, a USB stick, a flashcard, an SD card or the like.

A computer program comprises a program code for prompting the, in particular machine-induced, steps of the method, when the computer program runs on a computer, a computer program can be understood as, for example, a physical software product ready for distribution, which contains a program.

All or some of the, in particular machine-induced, steps of the method, may be prompted by the computer program product and the computer program.

Embodiments may possess some, several or all of the following features in any combination, unless the person skilled in the art recognizes the specific combination as technically impossible. Advantageous developments are each the subject-matter of the dependent claims as well.

In all of the following, the use of the expression "may be" or "may have" and so on, is to be understood synonymously with "preferably is" or "preferably has," and so on, respectively, and is intended to illustrate embodiments.

Whenever numerical words are mentioned herein, the person skilled in the art shall recognize or understand them as indications of numerical lower limits. Unless it leads the person skilled in the art to an evident contradiction, the person skilled in the art shall comprehend the specification, for example, of "one" encompassing "at least one". This understanding is also equally encompassed by the present disclosure as the interpretation that a numerical word, for example, "one" may alternatively mean "exactly one", wherever this is evidently technically possible for the person skilled in the art. Both are encompassed and apply herein to all used numerical words.

When an embodiment is mentioned herein, it then represents an exemplary embodiment.

A tolerated value, such as a tolerated diffusive sodium balance, may in some embodiments for example be considered as tolerated if it meets subjective and/or objective criteria.

Thus, the patient may specify that the diffusive sodium balance reached by the current or in one or several previous treatment sessions, e.g., after the end of treatment, was tolerated by him. Alternatively, the physician may determine based on his experience if the patient has tolerated the treatment(s) and in particular the diffusive sodium balance(s) reached thereby. Also alternatively, patient and physician may jointly conclude that the treatment(s) and in particular the diffusive sodium balances(s) have been tolerated. These possibilities count as, or encompass, subjective criteria.

Furthermore, objective criteria may be applied, which e.g., may be based on one or several measurable information. Theses may include vital parameters, postdialytic or intradialytic symptoms, the degree of vertigo, uneasiness, etc. which may be measured by measurement values or may be classified by gradings or in other ways.

When the diffusive sodium balance is mentioned herein, this is not to be understood as limiting. Although sodium may mostly influence the diffusive salt balance and plasma sodium may have the largest osmotic effect on blood, the present invention should however alternatively be further understood as follows: When the diffusive sodium balance is mentioned herein, other salts and/or osmotically active substances are also included in, or replace, the term "sodium balance". Instead of "sodium balance" and all terms related thereto, e.g., "salt balance" may also be used.

When sodium is mentioned herein, for example in connection with the diffusive sodium balance, this is not to be understood as limiting for another reason: here, sodium represents sodium as pure substance as well as each sodium salt or salt which comprises sodium, e.g., sodium chloride.

In several embodiments, the method may serve for, in particular stepwise, reducing the diffusive sodium balance.

In several embodiments, the method may serve for, in particular stepwise, reducing the ultrafiltration volume of one or several treatment sessions.

In certain aspects, a treatment method proceeds based on the treatment regimen previously determined by the method. This method may be understood as a planning method. Alternatively, the present invention does not relate to a treatment method.

The method for determining a treatment regimen may be carried out and completed thoroughly before the start of the treatment, i.e. for example before the first treatment session. It may alternatively be adapted during e.g., the first and the last treatment session. In this, an interaction with the patient is, however, not required. The patient does not have to be connected to a treatment apparatus during the adaptation. The presence of the patient is not required for the adaptation. The settings of the blood treatment apparatus for executing the blood treatment session need not to be changed during the current treatment session.

In several embodiments, the step of determining the transitional treatment regimen encompasses, or consists of, the following partial steps: determining (e.g., by the physician) that the diffusive total target sodium balance is preferably between −300 mmol and +300 mmol (here, it may possibly be that the positive sign is used with the removal from the patient, the negative sign is used with the administration to the patient) and further preferably it should be 0 mmol, determining (e.g., by the physician) or providing (e.g., using tables, patient file, etc.) a value of a target dry weight or of another target value of the weight of the patient (which should be sought e.g., by the dialysis upon the completion of the respective treatment session and/or which may serve as a treatment basis, e.g., for determining the ultrafiltration volume) for the first treatment session; determining (e.g., by calculation, reference table, patient's file) a value of an ultrafiltration volume to be removed by ultrafiltration (here in short: UF) during the first treatment session and which is, or would be, required for reaching the target dry weight or the other target value of the weight towards the end of the first treatment session; and specifying in advance an ultrafiltration volume by which the value of the ultrafiltration volume to be removed for reaching the target dry weight or the other target value of the weight of the first treatment session should be mathematically reduced.

In several embodiments, determining and/or assigning is detecting, entering, storing and/or calculating.

In several embodiments, the detecting is calculating or looking-up in a storage medium (table, list, etc.).

In several embodiments of the method, the ultrafiltration volume (may correspond to the ultrafiltration volume which is to be removed in order to achieve the dry weight) which has to be removed respectively for compensating the increase of the patient's weight that occurred due to diet intake since the last respective treatment session is increased respectively by a volume $V_{UF,extra}$ in a plurality of treatment sessions following directly or indirectly (i.e. without or with interruption) the treatment session denoted above as the "first" session. Thus, more weight is removed from the patient by ultrafiltration than (s)he has interdialytically (i.e. since the end of the last treatment session) gained by eating and drinking. In this, the volume $V_{UF,extra}$ is respectively smaller than the (adjusting) ultrafiltration volume $V_{UF,minus}$ by which the value of the ultrafiltration volume $V_{UF}(d)$ to be removed in order to reach the dry weight $m_{dry}$ or the other target value of the weight was mathematically reduced for the first treatment session (i.e. on day d=1).

In several embodiments, the steps mentioned in the preceding paragraph are repeated for a plurality of, in particular successive, future treatment sessions. The repetitions take place until the, over the plurality of treatment sessions summed-up, volumes $\Delta V_{UF,extra}$, by which was increased respectively, reach a total volume, which in turn reaches or exceeds the ultrafiltration volume $V_{UF,minus}$, by which the value of ultrafiltration volume to be withdrawn in order to achieve the target dry weight or the other target value was mathematically reduced for the upcoming treatment session.

In several embodiments, the step of determining the transitional treatment regimen encompasses or consist of the following step: determining a diffusive target sodium balance for a treatment session fixed for a predetermined day as $$M_{diff,target}(d) = M_{diff,tolerated}(d-1) - M_{diff,minus}(d)$$

wherein the following applies $M_{diff,\ target}(d)$ corresponds to a value of a diffusive sodium balance desired or determined during the upcoming treatment session BS_d;

$M_{diff,\ tolerated}(d-1)$ corresponds to a value of a diffusive sodium balance tolerated by the patient or qualified as tolerated during the or a previous (d'=d−1) treatment session (BS_d');

$M_{diff,\ minus}(d)$ corresponds to a determinable or determined value of a diffusive sodium balance by which $M_{diff,\ tolerated}(d-1)$ or $M_{diff,\ target}(d)$ is mathematically reduced.

In several embodiments, the following applies:

$$M_{diff,tolerated}(d-1) = M_{diff,target}(d-1)$$

wherein the following further applies:

$M_{diff,\ target}(d-1)$ corresponds for each value of d to the value of the desired, achieved or set diffusive sodium balance of the treatment session (BS_d−1) preceding the upcoming treatment session BS_d.

In several embodiments, the steps of the preceding paragraph are repeated for a plurality of, in particular successive, treatment sessions until the value of the diffusive sodium balance desired or set during the next treatment session reaches, or is less than, the diffusive total target sodium balance.

In several embodiments, the step of determining the transitional treatment regimen encompasses or consists of determining that the diffusive total target sodium balance $M_{diff,target\_total}$ should be between −300 mmol and +300 mmol, preferably it should be 0 mmol ("neutral diffusive sodium balance").

In several embodiments, the diffusive total target sodium balance $M_{diff,target\_total}$ is between −300 mmol and +300 mmol, preferably it is 0 mmol.

In certain embodiments, the blood treatment apparatus is designed as a peritoneal dialysis apparatus, hemodialysis apparatus, hemofiltration apparatus or hemodiafiltration apparatus, in particular as an apparatus for the chronic renal replacement therapy or for the continuous renal replacement therapy (CRRT).

In several embodiments, the blood treatment apparatus comprises sensors which are arranged upstream and/or downstream of a dialyzer of the blood treatment apparatus in order to measure the electrolyte balance and/or the liquid balance e.g., on the dialysis liquid side and/or on the blood side.

In some embodiments, the blood treatment apparatus comprises a control device or a closed-loop control device which may be programmed and/or configured to execute the method in interaction with further devices, in particular a blood treatment apparatus.

In several embodiments, the control device is configured to determine—based on information from the physician or the user—treatment parameters, in particular related to the ultrafiltration volume or the sodium concentration of the dialysis liquid, for one or several of the upcoming treatment sessions and/or to control or to regulate the treatment apparatus for a treatment based on these treatment parameters. The controlling or closed-loop controlling may optionally influence the dialysis liquid being mixed by an apparatus, e.g., the treatment apparatus, in particular its composition and/or its sodium content or sodium concentration.

The control device may be configured to send machine signals, which are directed as controlling signals to the treatment apparatus, based on input by the physician or—alternatively or additionally thereto—to create such machine signals based on stored algorithms. Hence, the physician may e.g., specify the treatment regimen to be followed and if applicable the framework conditions; the control device may adapt or determine the treatment parameters for individual or specific treatment sessions and send corresponding machine signals to the treatment apparatus.

The control device or closed-loop control device may be on-the-fly determined or changed, i.e. for example during the course of a treatment session or parallel to it. Alternatively, it may be determined and stored prior to the beginning of a treatment session and may be later on, e.g., during future treatment sessions, processed as stored.

The control device may be configured to store or to prompt the storing of input by the physician, algorithms for the calculation of machine signals and/or machine signals. Corresponding storage devices may be provided.

Corresponding and optionally (e)specially provided input fields, switches, controllers, etc. for the doctor may be comprised by the control device, by a display device and/or by a section of the blood treatment apparatus.

The control device may be configured to output—to the physician or user e.g., via display, via transmission to a receiver unit such as a smartphone or the like via a printout or the like—treatment parameters, in particular related to the ultrafiltration volume, a diffusive sodium balance or the sodium concentration of the dialysis liquid and/or treatment parameters adapted or determined by the control device.

In several embodiments, the control device or the treatment apparatus comprise devices which are configured to execute steps of the method. This applies for each step disclosed herein.

In several embodiments, the method may encompass individual or arbitrarily combined steps of the following exemplary embodiment:

The patient's dry weight $m_{dry}$ and the associated total body water volume $V_{TBW,\ dry}$ are determined by a suitable method, e.g., by bioimpedance measurement or by a clinical method and/or by using anthropometric formulas. The dry weight $m_{dry}$ usually represents the target weight to be achieved by liquid removal at the end of the dialysis session.

Furthermore, the respective diffusive sodium balance $M_{diff}$, e.g., between blood compartment and dialysis liquid compartment of the dialyzer, is determined based on previous treatment sessions which already took place prior to the beginning of the method and in which the patient had been symptom-free and/or which is considered as tolerated. In this context, the following parameters are parameters of the treatment session, each of which may optionally be taken into account:

Date d of the treatment session: is crucial for long (e.g., with a treatment break of two days) or short (e.g., with a treatment break of only one day) interdialytic interval, fluctuations in the biorhythm of the patient, etc.

Intradialytic symptoms ξ: indicate the tolerance of the patient to the treatment regimen.

Predialytic plasma sodium concentration $c_{plasma,\ pre}$, as the sodium concentration in the blood measured prior to the beginning of a treatment session: is relevant for the gradient of the sodium concentration between blood and dialysis liquid and influences the diffusive sodium transfer; it may also be a diagnostic parameter. This determination without the need of blood samples is described in EP 3 183 013 A1. Other determination methods are also possible.

Medium dialysis liquid sodium $\bar{c}_{di}$ during the dialysis session: the gradient between blood and dialysis liquid influences the diffusive sodium transfer. $\bar{c}_{di}$ usually is constant during the treatment session. It may vary during the dialysis session due to adjustments of the user, change in the sodium profile or automated closed-loop controls of the dialysis liquid sodium.

Dialysis dose $Kt/V_{TBW}$: decisive for the amount of diffusive mass or molecule transfer for a given concentration gradient.

Ultrafiltration volume $V_{UF}$: volume of the liquid removal for the partial or complete compensation of the overhydration.

Kt/V is a parameter for determining the dialysis effectiveness. K is the clearance, it is determined by the urea content of the blood before and after the dialysis. t is the effective dialysis time in minutes. For example, V may be set at 60% of the body mass (weight) in which the blood may circulate (body water content).

These parameters may be combined into a parameter set $\Psi_j = \{d,\ \xi,\ M_{diff},\ c_{plasma,\ pre},\ \bar{c}_{di},\ Kt/V_{TBW},\ V_{UF}\}$ for each treatment session. Other parameter sets are also contemplated and may describe a specific treatment session.

The determination of the diffusive sodium balance $M_{diff}$ between blood compartment and dialysis liquid compartment of the dialyzer or in the peritoneal dialysis is e.g., described in EP 2 413 991:

$$M_{diff}(t) = \int_{\tau=0}^{t} c_{di}(\tau - t_f)Q_d(\tau - t_f)d\tau - \int_{\tau=0}^{t} c_{do}(\tau)Q_d(\tau)d\tau \qquad \text{Formula 1}$$

$t_f$ denotes the middle flow time (i.e. the delay time), which a volume element requires for the way from the measuring point of $c_{di}$ to the measuring point of $c_{do}$.

In this, the points $c_{di}$ and $c_{do}$ represent e.g., the sodium concentration in the dialysis liquid upstream respectively in the dialysate downstream of the dialyzer respectively in the fresh respectively used peritoneal dialysis liquid. These may be determined by suitable ion selective sensors.

$Q_d$ denotes the total flow of the fresh dialysis liquid, comprising the liquid flow through the dialysis liquid compartment of the dialyzer and the liquid flow possibly branched off with substitution methods (hemofiltration (HF), hemodiafiltration (HDF)).

Alternatively, the temperature-compensated total conductivity σ may be measured in order to determine the sodium concentration and, from this, taking into account the composition of the dialysis liquid, the sodium concentration at the respective measuring point may be deduced.

$$\sigma = f(c_{Na^+},\ c_{K^+},\ \dots) = \sum_j c_j \gamma_j + \sigma_{Ofs} \qquad \text{Formula 2}$$

$$\Rightarrow c_{Na^+} = \frac{1}{\gamma_{Na^+}}\left(\sigma - \sum_{j \neq Na^+} c_j \gamma_j + \sigma_{Ofs}\right)$$

This linear relationship is, to a good approximation, valid in the concentration ranges relevant for the dialysis, wherein $c_j$ denotes the concentration of all ions contributing to the total conductivity, $\gamma_j$ denotes their known specific conductivity and $\sigma_{Ofs}$ denotes an offset originating from the linearization.

While the composition for the fresh dialysis liquid upstream of the dialyzer is known because of the knowledge of the used concentrates and the settings at the dialysis device with respect to the mixing ratios, the composition of the used dialysate downstream of the dialyzer is not known a priori because of the mass transfer between blood and dialysis liquid in the dialyzer. For it, the concentration of sodium and/or the ions contributing to the conductivity in addition to sodium may be determined by suitable measuring methods or, as described in EP 2 413 991 A1, by a kinetic model for the concentration course of the relevant ions in blood and in the dialysate downstream of the dialyzer.

In several embodiments, rules for the provision of symptom-free treatments at or with a specific value of the diffusive sodium balance $M_{diff}$ may be derived—for example by using methods of the time series analysis, e.g., from the parameter sets $\Psi_j$—for a definable, representative, previous time period. The aim is to determine the specific value of the diffusive sodium balance $M_{diff,\ tolerated} = f(\Psi_j)$ from the historical data which allows symptom-free treatment regardless of the procedure for a treatment day d of the transitional phase or of the transitional regimen lying between the previous procedures and therefore before executing the method, wherein by the method a transfer will take place from the previous treatment regimen (here: Regimen 1, i.e. for example the standard treatment) into the desired treatment regimen in which a treatment with the diffusive target sodium balance will be carried out (here: Regimen 2, i.e. a treatment regimen with reduced or closed-loop controlled dialysis liquid natrium).

In the simplest case $M_{diff,\ tolerated}$ (Regime1) is provided by the average value of $M_{diff}$ in the relevant past time period. Periodic fluctuations of $M_{diff}$ are however also possible, when, for example on treatment days after the long interdialytic interval with which a higher ultrafiltration volume (in short: UF volume) was removed, a higher medium dialysis liquid sodium was prescribed by the user in order to avoid symptoms. Likewise, periodic fluctuations of $c_{plasma,\ pre}$ are possible in the range of weeks due to the biorhythm of the patient. Since changes of $c_{plasma,\ pre}$ with constant dialysis liquid sodium influence the diffusion gradient, they result in periodic fluctuations of $M_{diff}$.

Other determinations of $M_{diff}$, which are partially not related to $\Psi_j$, are likewise possible.

In several embodiments, a target value for the diffusive sodium balance $M_{diff,\ target}$ (Regime 2) to be achieved is specified for the intended treatment regimen of the patient, herein the target value is denoted as diffusive total target sodium balance $M_{diff,\ target\_total}$. It is determined how to achieve the transition between these two regimens. For this purpose, a calculation method or a rule is specified, according to which the liquid removal taking place in the transitional phase or the transitional regimen encompassing several treatment sessions should deviate from the UF volume $V_{UF}(d)$ required to achieve the dry weight $m_{dry}$, and the diffusive sodium balance should deviate from the desired diffusive sodium balance.

The statements made herein may also be applied to hemo(dia)-filtration and peritoneal dialysis.

For example, Formula 1 (top) may be generalized to the effect that there is no volume removal during substance or mass transfer. Formula 1 thus remains unchanged also for hemofiltration in which dialysis liquid is mixed online, i.e. by the treatment machine, and is applicable in both pre- and post-dilution operation.

For peritoneal dialysis and for the hemofiltration with dialysis liquid from bags and without liquid removal, $M_{diff(t)}$ would practically be the integration of Formula 1:

$$M_{diff(t)}=(d_{di}-c_{do})*V.$$

With liquid removal (i.e. with volume removal using the ultrafiltration pump or with the peritoneal dialysis by osmosis) the following applies for the diffusive total sodium balance $M_{ges}=c_{di}V_{di}-c_{do}V_{do}$.

with $V_{do}=V_{di}+V_{UF}$ the result is then $$M_{ges}=M_{diff}-c_{do}V_{UF}.$$

In case of known infusion volume or inlet volume $V_{di}$, the diffusive sodium balance, which causes a change in the sodium concentration in the blood, may here also be calculated.

In online hemo(dia)filtration methods, the diffusive sodium balance is decoupled from the removal of uremic toxins (such as urea), since the sodium concentration of the dialysis liquid and with it the sodium concentration gradient determining the mass transfer may be varied. However, in methods with which the dialysis liquid originates from bags, the sodium concentration of the dialysis liquid is determined from the outset. The sodium transfer may therefore only be actively influenced by variation of the dialysate flow or the duration of treatment. Simultaneously, these measurements also relate to the removal of uremic toxins.

Alternatively, a specific (manual or automatic) change of bags with dialysis liquids of different sodium concentration is possible, which is also provided as an option and e.g., may be provided in the treatment plan. Although such changes lead to fluctuations in the sodium balance during the treatment session, points in time for changing the bags and dialysate flows may be determined such that the desired diffusive sodium balance is achieved at the end of the treatment, due to sufficiently frequent measurement of $c_{do}$ by known sodium concentration of the bag content. This applies both to hemofiltration by bag and to peritoneal dialysis.

To this end, the use of a kinetic model of mass transfer with respect to the sodium concentration of the bag content and the measurement of $c_{do}$ would further be advantageous for determining the point(s) in time for the bag change necessary for achieving the diffusive sodium balance.

In some embodiments, the method runs on a computer. For input, an input facility may be provided for the user. To display the results of the method or treatment instructions, output devices or display devices may be provided.

In several embodiments, the method encompasses the determining or quantifying of a diffusive sodium balance that has been qualified and/or quantified as tolerated diffusive sodium balance in one or several preceding treatment sessions of the patient.

In some embodiments, the diffusive sodium balance is determined from the volume of distribution V or $V_{TBW}$ of the patient (corresponds to the "water content") and the change in the sodium concentration in mmol/l. In a typical patient with V=40 l, an intradialytic increase in the plasma sodium concentration by 1 mmol/l namely means a diffusive sodium balance of −40 mmol. Intradialytic changes in sodium concentration are typically between +/−3 mmol/l, changes by more than 6 mmol/l are rare, at the most when administering sodium to hyponatremic patients.

Some or all embodiments may include one, several or all of the above-mentioned and/or in the following stated advantages.

An advantage is easy implementation, which requires neither the measurement of values such as of the relative blood volume nor a course to avoid intradialytic complications.

Since such values do not have to be measured, there is no need for the provision of any, possibly additional, devices for this purpose on the dialysis machine, e.g., in form of optical sensors or ultrasound sensors, especially adapted blood tubing systems or the like.

In practice, the current relative blood volume or its rate of change is regularly compared with an individually defined patient's threshold and the rate of the liquid removal is reduced when the threshold value is exceeded. This may lead to the fact that permanently at the end of dialysis, the volume of liquid removed is less than planned and thus the dry weight is not reached. These circumstances are advantageously avoided.

Typically, in the prior art, the reaction to a drop of the relative blood volume is the increase of the dialysis liquid sodium. This leads to an (increased) salt intake to the patient, so that the original aim of reducing both the dialysis liquid sodium and the salt intake is not achieved. Also, these circumstances are advantageously avoided.

Advantageously, a method and an apparatus are further presented to manually or automatically extend the transition between different treatment regimens or the treatment with a new treatment regimen and with a diffusive total target sodium balance over several consecutive treatments in such a way that after the transitional phase or transitional regimen, the desired, new treatment regimen is achieved as symptom-free as possible. Such embodiments may not include additional devices at the dialysis machine or especially adapted tube systems.

Advantageously, the method may effect that the sodium concentration in the dialysis liquid may be chosen such that in the dialyzer there is no diffusive gradient anymore between blood and dialysis liquid. This allows an automatic individualizing of the sodium concentration, as described e.g., in the EP 2 413 991 A1.

It may also be advantageous that an individualization of the sodium concentration in the dialysis liquid is possible even if the patient was treated in the previous treatment regimen with a center-specific constant sodium concentration.

Advantages of the method are particularly evident in patients with a plasma sodium concentration, which is regularly significantly lower than that of the dialysis liquid sodium. With the patients the now possible individualization of dialysis liquid sodium leads to a reduction of dialysis liquid sodium. The same happens when the standard for the dialysis liquid sodium of the sought dialysis center is generally reduced due to external requirements, e.g., due to efforts to reduce the intradialytic salt intake to the patient in general.

The methods for determining and/or applying a treatment regimen reduce or eliminate the need for intradialytic salt administration.

If now the dialysis liquid sodium is reduced due to manual specifications or by automated individualization after a previous treatment with significantly higher dialysis liquid sodium, then, advantageously for the patient, the following unfavorable combination is omitted: In the previous treatment, an intradialytic salt intake took place because of the increased dialysis liquid sodium compared to the plasma sodium, which led to an increased liquid intake, which is now to be compensated in the current dialysis by increased liquid removal. Due to the concurrent reduction of the dialysis liquid sodium, there is now however a lack of osmotic support for the flow of body water into the blood vessels. Thus, at such a coincidence of increased ultrafiltration volume (short: UF volume) and reduced dialysis liquid sodium, the patient is particularly vulnerable to intradialytic symptoms such as blood pressure drops and convulsions. Using the method, the consequences may be advantageously avoided or at reduced. In certain embodiments, all advantages achievable with the method may be also achieved in an undiminished manner with the apparatuses.

In the following, the present invention is exemplarily described with regard to the accompanied figures in which same reference numerals refer to similar or the same components. The following applies:

DETAILED DESCRIPTION OF THE FIGURES

Figure 1:
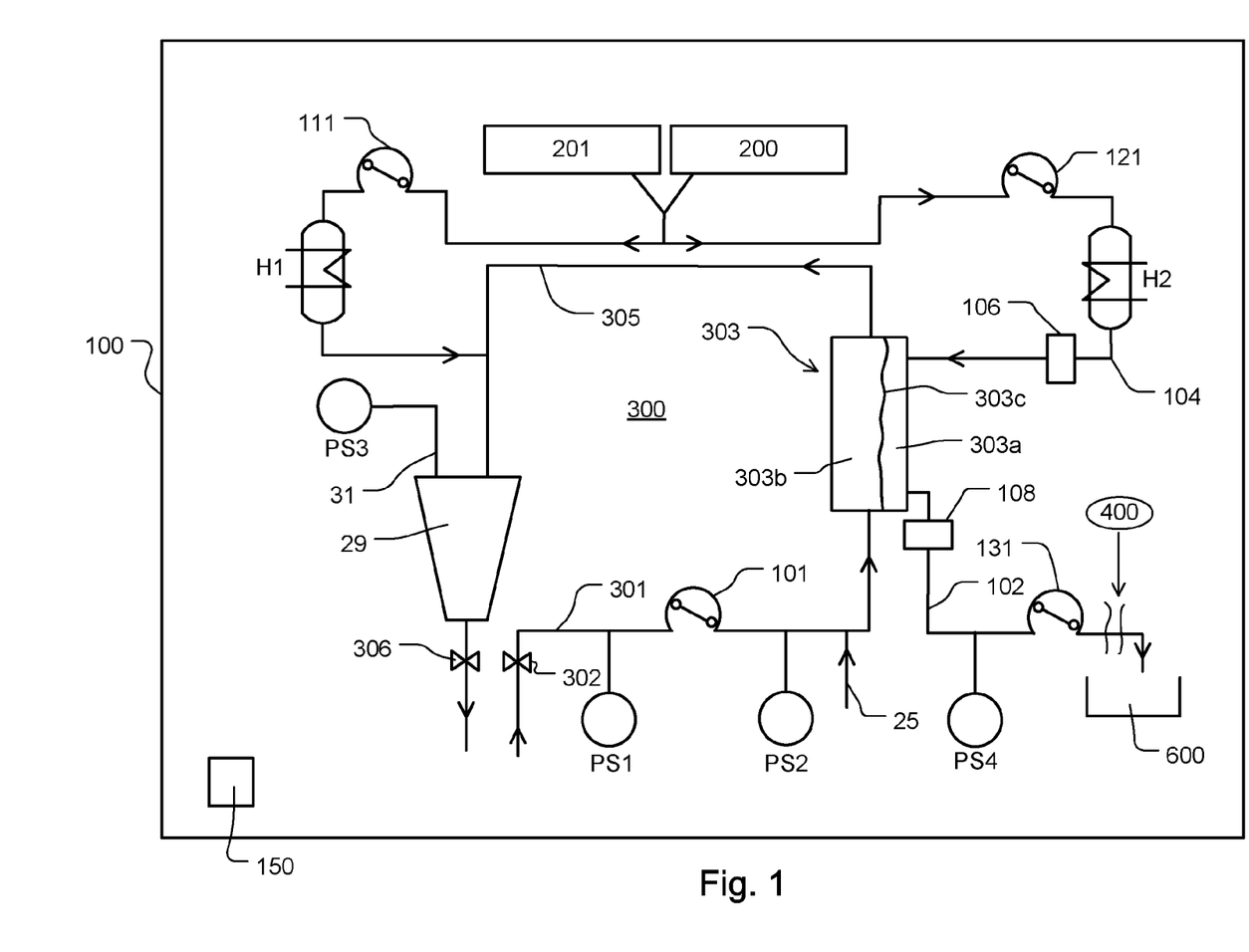
FIG. 1 shows a simplified illustration from a blood treatment apparatus having an extracorporeal blood circuit in a first embodiment.

FIG. 1 shows a greatly simplified illustration of a blood treatment apparatus 100 connected to an extracorporeal blood circuit 300 and an only indicated discharge hose system having an effluent bag 400.

The extracorporeal blood circuit 300 comprises a first line 301 here an arterial line section.

The first line 301 is in fluid communication with a blood treatment apparatus, here exemplarily a blood filter or dialyzer 303. The blood filter 303 comprises a dialysis fluid chamber 303a and a blood chamber 303b, which are separated from each other by a mostly semi-permeable membrane 303c.

The extracorporeal blood circuit 300 further comprises at least a second line 305, here a venous line section. Both the first line 301 as well as the second line 305, can serve as connection to the patient's vascular system (not shown).

The first line 301 is optionally connected with a (first) hose clamp 302 for blocking or closing line 301. The second line 305 is optionally connected with a (second) hose clamp 306 for blocking or closing line 305.

The blood treatment apparatus 100 which is represented, only by some of its devices and merely schematically, in FIG. 1, comprises a blood pump 101. During the patient's treatment, the blood pump 101 conveys blood towards the blood filter or dialyzer 303. This is illustrated by the small arrows, which are used in each of the figures to generally indicate the direction of flow.

Fresh dialysis liquid is pumped from a source 200 along the dialysis liquid inlet line 104 into the dialysis liquid chamber 303a, by a pump for dialysis liquid, which may be designed as a roller pump or as an otherwise occluding pump. The dialysis liquid leaves the dialysis liquid chamber 303a in the direction of the basin 600 as dialysate possibly enriched by filtrate, and is herein referred to as effluent.

The source 200 may be, for example, a bag or a container. The source 200 may also be a fluid line through which online and/or continuously generated or mixed liquid is provided, for example, a hydraulic output or connection of the blood treatment apparatus 100.

A further source 201 with substitute may be optionally provided. It may correspond to the source 200 or be a separate source. The substitute may be optionally heated, e.g., in the optional bag heating H1.

In addition to the aforementioned blood pump 101, the arrangement in FIG. 1 further includes an optional series of further pumps. The series of pumps include the pump 111 for substitute, the pump 121 for dialysis liquid, and the pump 131 for the effluent, each pump being optional.

The pump 121 is provided to supply dialysis liquid from a source 200, for example a bag, via an optional existing bag heater with a bag H2 to the dialyzer 303, via a dialysate liquid inlet line 104.

The supplied dialysis liquid exits from dialyzer 303 via a dialysate outlet line 102, supported by the pump 131, and may be discarded.

Upstream of the blood pump 101, an optional arterial sensor PS1 is provided. During a patient's treatment it measures the pressure in the arterial line.

Downstream of the blood pump 101, but upstream of the blood filter 303 and if provided, upstream of an addition site 25 for heparin, a further optional pressure sensor PS2 is provided. The pressure sensor PS2 measures the pressure upstream of the blood filter 303 ("pre-hemofilter").

Again, a further pressure sensor to measure the filtrate pressure or the membrane pressure of the blood filter 303 may be provided as PS4 downstream of the blood filter 303, however, preferably upstream of the pump 131 in the dialysate outlet line 102.

Blood, which leaves the blood filter 303, passes through an optional venous blood chamber 29, which may comprise a ventilation device 31 and can be in fluid communication with a further pressure sensor PS3.

The exemplary arrangement shown in FIG. 1 comprises a control or closed-loop control device 150. It may be in cable or wireless signal communication to any of the components referred to herein—in particular or at least to the blood pump 101—in order to control or regulate the blood treatment apparatus 100. It is optionally configured to carry out the herein described method.

Alternatively to the embodiment shown herein, the blood treatment apparatus may comprise a device for the online mixing of dialysis liquid consisting of a plurality of components which may include an acidic concentrate, a bicarbonate component and reverse osmosis water.

Using the device for the online mixing, a variation of the sodium content of the dialysis liquid, controlled by the control device 150, is possible within certain limits.

Furthermore, the blood treatment apparatus 100 optionally comprises a device for the exact balancing of the dialysate flow flowing into and out of the dialyzer 303.

The blood treatment apparatus 100 further comprises devices, such as an ultrafiltration pump 131, for the exact removal of a liquid volume $V_{UF}$, predetermined by the user and/or by the control device 150, from the balanced circuit.

Sensors 106 and 108 serve to determine the conductivity, which is in some embodiments temperature-compensated, and the liquid flow upstream and downstream of the dialyzer 303. The sensors 106, 108 may also be a suitable, and having the same effect, combination of actuators such as calibrated pumps, balancing chambers and pressure sensors. Instead of an optional determination of the temperature-compensated conductivity, devices for ion-selective measurement are optionally also possible.

Based on the measurement of the sensors 106 and 108, the control device 150 determines, in some embodiments, the electrolyte and/or liquid balance. Also, the control device 150 optionally determines, based on user specifications and stored algorithms, the default value for the electrolyte and liquid balance, in particular the diffusive target sodium balance $M_{diff,\ target}$ (d) and/or the diffusive total target sodium balance $M_{diff,\ target\_total}$, to be achieved in the ongoing or current treatment.

User specifications and/or the display of calculated values and/or the treatment of progress are possible via an optional user interface (not shown).

An internal or external computing unit and/or storage unit (not shown) may also be provided. It may be able to store and evaluate the historical data necessary for calculating the current electrolyte and liquid balance. In this, for example, it may only provide the raw data for a calculation running in the control device 150. Alternatively, the calculation in the computing unit and/or storage unit (not shown) may also already be carried out based on an algorithm, e.g., implemented in it, such that only the end result from the computing unit and/or storage unit (not shown) is transmitted in form of guidelines specification to the control device 150.

Although the blood treatment apparatus is shown in FIG. 1 as an apparatus for hemo(dia)filtration, however, peritoneal dialysis apparatuses are also contemplated, even though not specifically illustrated by a figure.

Figure 2:
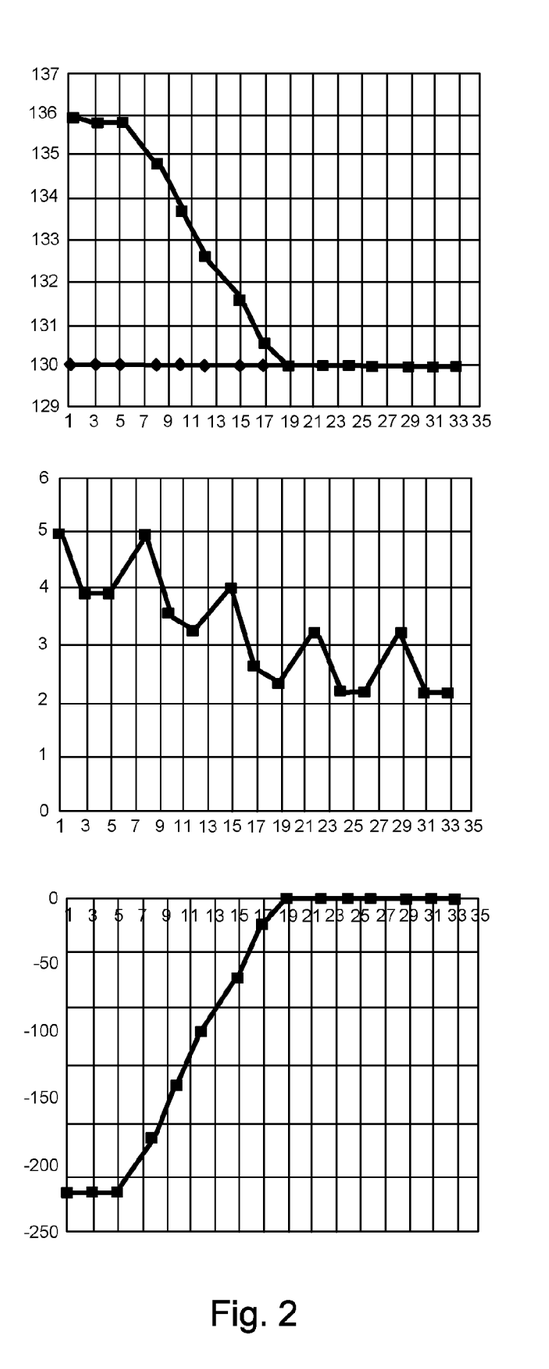
FIG. 2 shows a simulation of the tracking of the deviation from the diffusive sodium balance in an embodiment.
Figure 3:
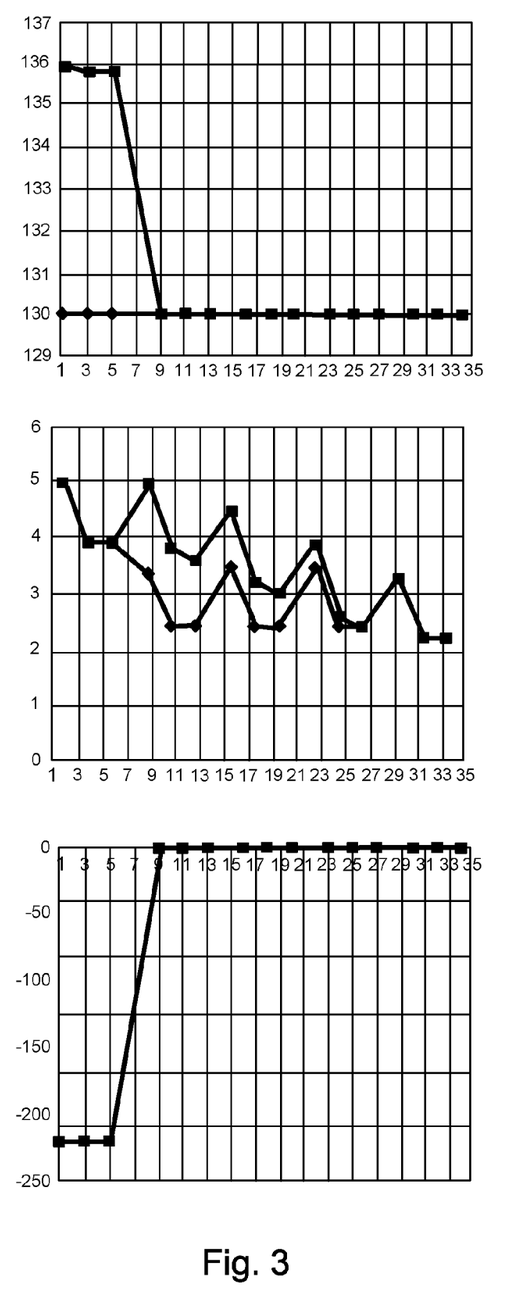
FIG. 3 shows another simulation of the tracking of the deviation from the UF volume in another embodiment.

FIG. 2 and FIG. 3 show in simulations, how a patient is stepwise continuously or progressively transferred over a transitional period of several days d from a previous regimen, the treatment regimen 1, in which the patient is being treated, in FIG. 2 and FIG. 3 until (including) day 5, with a high dialysis liquid sodium—relative to the patient's plasma sodium—to the desired or new treatment regimen, the regimen 2, comprising a dialysis liquid sodium which is low or adapted to the patient's plasma sodium, which regimen 2 begins on day 19 (FIG. 2) and on day 27 (FIG. 3).

It is assumed that the model patient has a distribution volume $V_{TBW}$ of 40 l, ingests 140 mmol NaCl through diet each day, is dialyzed three times a week (e.g., Monday, Wednesday, Friday) and drinks so much liquid between each treatment sessions that his plasma sodium reaches the setpoint of 130 mmol/l before the next dialysis or treatment session.

In the simulations, until the beginning of the fourth treatment, (day 8, which corresponds to d=1, after the long interval, i.e. on Monday, i.e. with two dialysis-free days (Saturday and Sunday) instead of one dialysis-free day such as between Monday and Wednesday or Wednesday and Friday) the previous treatment regimen or the standard regimen is assumed as follows. Due to the constant concentration of the dialysis liquid sodium, the patient's plasma sodium is raised to ca. 130 to 138 mmol/l under consideration of the typical dialysis efficiency for his treatment. The herewith associated diffusive salt transfer is determined using the sensors 106, 108 of the blood treatment apparatus 100. The UF volume $V_{UF}$ is adjusted, respectively, so that the liquid feed triggered by the salt ingestion is completely balanced again between the treatment sessions. Therefore, UF volume and predialytic overhydration in regimen 1 are identical. Thus, the patient reaches his dry weight $m_{dry}$ at the end of each treatment regimen. This previous treatment session was tolerated free of symptoms by the patient. The values for dry weight $m_{dry}$ and intradialytic diffusive NaCl removal are stored during this previous treatment regimen 1. An averaging of $M_{diff}$ over one week results in a diffusive sodium infusion of 220 mmol (see the bottom illustration of FIGS. 2 and 3), so that in this case $M_{diff,tolerated}$=220 mmol.

FIG. 2 shows the tracking of the deviation from the diffusive sodium balance in a simulation of the method.

FIG. 2 (top) shows the plasma sodium [mmol/l] over consecutive days, which also include the treatment days d, wherein the predialytic sodium of the plasma is indicated by small diamonds, the postdialytic plasma by squares.

FIG. 2 (middle) shows the ultrafiltration volume UF [l] over the consecutive days. In this, the ultrafiltration volume UF [l] corresponds to the respective, intradialytic weight increase on each day of the treatment.

FIG. 2 (bottom) shows the diffusive sodium balance over consecutive days, respectively.

FIG. 2 illustrates the step-by-step achievement of a diffusive intradialytic sodium zero-balance as an example of a desired diffusive total target sodium balance $M_{diff,\ target\_total}$. In FIG. 2, the dialysis liquid sodium is stepwise adapted.

For the patient, the physician determines by which amount $M_{diff,\ minus}$ (d) at each treatment session should be deviated from the diffusive sodium balance $M_{diff,\ tolerated}$ (d−1) tolerated in the respective previous treatment session BS_d−1 towards the balancing target in the transitional treatment regimen.

In general, this results in a target value, either in this way or in another way, for each treatment day d, the value may be as follows for the diffusive intradialytic sodium balance:

$$M_{diff,target}(d)=M_{diff,tolerated}(d-1)-M_{diff,minus}(d) \qquad \text{Formula 3}$$

In the simplest case, $M_{diff,\ minus}$ (d) may be a constant value. This amount may be expressed as an absolute amount (in mmol or g) or an expected change in the concentration of postdialytic plasma sodium $c_{plasma,\ post}$. For example, it may be medically assumed that a deviation of the plasma sodium concentration at the end of the dialysis session (i.e. the postdialytic plasma sodium concentration $c_{plasma,\ post}$) by 1.0 mmol/l from the final value reached in the tolerated previous treatment regimen (regimen 1) is possible without symptoms. In this case, it would be $$M_{\textit{diff,minus}}(d) = V_{TBW} * 1.0 \frac{\text{mmol}}{1},$$

thus, it is 40 mmol in the present example.

The approximation to the desired treatment regimen (regimen 2) then results, e.g., from the iteration:

$$M_{\textit{diff,tolerated}}(d) = M_{\textit{diff,target}}(d-1) \qquad \text{Formula 4}$$

This iteration is repeated until the following applies:

$$M_{\textit{diff,target}}(d) = M_{\textit{diff,target}}(\text{Regime 2}) = M_{\textit{diff,target\_total}}.$$

Generally however, e.g., in case of oscillation of $M_{\textit{diff, tolerated}}$ (d) in the previous treatment regimen (regimen 1), complicated courses of $M_{\textit{diff, tolerated}}$ (d) when approximating $M_{\textit{diff, target}}$ (Regime 2) are possible.

In the transitional phase or the transitional regimen (starting with day 8), instead of a fixed specification of the dialysis liquid sodium a regulation of the dialysis liquid sodium based on the balancing of the salt transfer between blood and dialysis liquid is now activated, as described in EP 2 413 991 A1. This regulation measures, preferably continuously, the salt balance at the dialyzer 303 and regulates the dialysis liquid sodium in such a way that respectively at the end of the current treatment session BS_d, the predetermined target value $M_{\textit{diff, target}}$ (d) for the salt transfer of this treatment session is reached. Since in the present example the intradialytic diffusive salt intake becomes always smaller, the plasma sodium increases during the treatment session less from session to session. The patient has to drink less between treatment sessions as a physiological reaction, so that the interdialytic weight increase (i.e. between two consecutive treatment sessions) and thus the UF volume $V_{UF}$ (d) to be prescribed in the following treatment session continuously decreases. Thus, the above-described critical concurrence of a high UF volume with the abrupt discontinuation of the intradialytic diffusive salt intake along with the known associated symptoms are avoided.

At the end of the transitional phase or the transitional regimen (starting from day 19), a new osmotic equilibrium without intradialytic diffusive salt intake and with low UF volume is achieved in the new regimen (the desired treatment regimen).

FIG. 3 shows the tracking of the deviation of the UF volume in another simulation of the method.

FIG. 3 (top) shows the plasma sodium [mmol/l] over consecutive days which encompass also the treatment days d, wherein the predialytic sodium of the plasma is indicated by small diamonds, the postdialytic plasma by squares.

FIG. 3 (middle) shows the ultrafiltration volume UF [1] (indicated by small diamonds) and the overhydration (indicated by squares) over the consecutive days.

FIG. 3 (bottom) shows the diffusive sodium balance over the consecutive days, respectively.

In FIG. 3 the dialysate sodium is adapted to the plasma sodium already from day 8 (inclusive) continuing from then until the last treatment session of the method. Hereby, the ultrafiltration volume UF[1] is tracked stepwise.

Thus, FIG. 3 shows another way to avoid the critical concurrence of a high UF volume with the discontinuation of the intradialytic diffusive salt intake. This procedure proposes, when stopping the salt intake on treatment day d=1, to decrease the UF volume $V_{UF}$, contrary to the usual setting at which the patient would reach his dry weight $m_{dry}$ at the end of the treatment session (see FIG. 3). However, this reduction causes that the patient does not reach his dry weight $m_{dry}$ at the end of the treatment session BS_d. Instead, the missing ultrafiltration volume is distributed over the following treatment sessions BS_d (with d=2, ..., n) in which, in addition to balancing of the interdialytic weight increase $V_{IDWG}$, the associated overhydration $V_{OH}$ is reduced gradually.

The reduction of the UF volume $V_{UF}$ which has to be undertaken at the beginning and/or during the transitional phase or the transitional regimen may be determined by various physiological models.

Most simply, a volume of liquid is calculated or otherwise determined (e.g., via a table) for the amount of salt diffusively administered in the previous treatment sessions, which volume of liquid compensates the salt intake such that the concentration of plasma sodium remains unchanged. If $M_{\textit{diff, tolerated}}$ (Regime 1) and $c_{\textit{plasma, pre}}$ (Regime 1) have been determined in regimen 1, optionally depending on the parameter constellation $\Psi_j$, then the reduction of UF volume $V_{UF, \textit{minus}}$ is as such $$V_{UF,\textit{minus}} = \frac{M_{\textit{diff,tolerated}}(\text{Regime 1})}{c_{\textit{plasma,pre}}(\text{Regime 1})} \qquad \text{Formula 5}$$

Alternatively, models which determine e.g., the osmotic volume shift between intra- and extracellular volume (see Guyton & Hall, Textbook of Medical Physiology) are possible:

Predialytic bioimpedance measurements are used to determine extracellular and intracellular volume $V_{EC}$ and $V_{IC}$ as well as total body water volume $V_{TBW}$ and the overhydration $V_{OH}$.

For the total body water volume $V_{TBW}$ the following applies $$V_{TBW} = V_{EC} + V_{IC} \qquad \text{Formula 6}$$

Considering the simplification that only sodium chloride contributes to osmolality, the latter is in each compartment (EC and IC) equal to twice the respective sodium concentration:

$$c_{\textit{osm},j} = 2c_j \qquad \text{Formula 7}$$

In the osmotic equilibrium, the following applies:

$$c_{\textit{osm,EC}} = c_{\textit{osm,IC}} = c_{\textit{osm,TBW}} \qquad \text{Formula 8}$$

$$\frac{M_{EC}}{V_{EC}} = \frac{M_{IC}}{V_{IC}}$$

At constant total body water volume, the osmolality in the total body water TBW changes by $M_{\textit{diff}}$ due to the change in the amount of sodium caused by the dialysis $$\hat{c}_{\textit{osm,TBW}} = c_{\textit{osm,TBW}} + \frac{2M_{\textit{diff}}}{V_{TBW}} \qquad \text{Formula 9}$$

In the new osmotic equilibrium the following applies because $$\hat{c}_{\textit{osm,TBW}} = c_{\textit{osm,TBW}} \qquad \text{Formula 10}$$

$$\hat{V}_{EC} = V_{TBW} \frac{V_{EC} c_{\textit{osm,TBW}} + 2M_{\textit{diff}}}{V_{TBW} c_{\textit{osm,TBW}} + 2M_{\textit{diff}}}$$

with that, the extracellular volume changes by $$\Delta V_{EC} = \hat{V}_{EC} - V_{EC} = V_{TBW} \frac{V_{EC} c_{osm,TBW} + 2M_{diff}}{V_{TBW} c_{osm,TBW} + 2M_{diff}} - V_{EC} \quad \text{Formula 11}$$

Thus, in a complete omission of the diffusive intradialytic salt intake, the UF volume should be reduced by $V_{UF,minus} = \Delta V_{EC}$.

The described, greatly simplified osmotic model may be extended to include other osmotically active substances as well as volume and substance removal by ultrafiltration.

When the volume withdrawal is reduced by $V_{UF,minus}$ in the first treatment session BS_d on day d=1 of the transitional phase or the transitional regimen (corresponds to day 8 in FIG. 2 or FIG. 3), the patient is overhydrated about $V_{UF,minus}$ at the end of the dialysis session. This overhydration is stepwise reduced in the following dialysis sessions.

For this purpose, e.g., a priori, a liquid volume $V_{UF,extra}$ may be determined for the patient. the liquid volume $V_{UF,extra}$ should be additionally withdrawn from the patient in each dialysis session; it is namely to be additionally withdrawn in addition to the already required balance $V_{UF}$ of the interdialytic weight increase.

This may be a fixed value or a value which is determined in relation to a maximum tolerated ultrafiltration volume $V_{UF,max}$, e.g., determined from the time-series analysis of the parameter sets $\Psi_j$ in the previous treatment regimen, the regimen 1.

Alternatively, this volume $V_{UF,extra}$ may be dynamically determined, e.g., by observing the relative blood volume RBV, wherein in each treatment as much volume is withdrawn until either a critical value of the RBV, a maximum value of $V_{UF,extra}$ or the dry weight $m_{dry}$, in particular calculated, is reached. The maximum value of $V_{UF,extra}$ may be e.g., a patient-specific or a center-specific definition. It may be specified by the user. The maximum value may be reached if a maximum ultrafiltration rate, determined by a specified ultrafiltration volume and the duration of treatment, is reached. Alternatively, the maximum ultrafiltration rate may be technically limited by the dialysis machine or will be limited for medical reasons. An example of the latter option is e.g., 10 ml/min/kg body weight.

Basically, the interdialytic weight increase or liquid increase $V_{IDWG}$ between the end of the dialysis on the previous treatment day d−1 and the beginning of the dialysis on the treatment day d is required in order to prescribe the UF volume $V_{UF}$:

$$V_{IDWG} = [m_{pre}(d) - m_{post}(d-1)] \frac{1}{kg} \quad \text{Formula 12}$$

If the patient in the previous treatment regimen (regimen 1) has reached his dry weight $m_{dry}$ at the end of the dialysis session on the treatment day d−1, he will also reach it by the prescription $V_{UF} = V_{IDWG}$ on the following treatment day d.

The following applies for the predialytic overhydration $V_{OH}$ of the patient on treatment day d.

$$V_{OH} = [m(d) - m_{dry}] \frac{1}{kg} \quad \text{Formula 13}$$

Therefore, m(d) corresponds to the weight of the patient on day d before the beginning of the dialysis session.

In FIG. 3, as an example, a linear return to the dry weight $m_{dry}$ at a constant value of $V_{UF,extra} = 0.21$ is illustrated:

On the first day d=1 of the transitional regimen (or the transitional phase), in which e.g., a diffusive sodium zero balance ($M_{diff,\ target\_total} = 0$ mmol/l) is prescribed, a reduced UF volume $$V_{UF}(d) = V_{IDWG} - V_{UF,minus}$$

is prescribed. Due to the omitted intradialytic salt supply to the patient starting from this treatment session BS_d (with d=1), the liquid intake, starting from this treatment session, is already reduced in the interdialytic interval (i.e. until the treatment session BS_d+1) and is only determined by the salt content of the intradialytic nutrition or ingested by the patient. However, as the patient was still overhydrated by $V_{UF,minus}$ at the end of the treatment, the interdialytic liquid increase $V_{IDWG}$ determined one the following treatment day d+1 is less than the measurable overhydration $V_{OH}$. There will be now prescribed an UF volume $$V_{UF} = V_{IDWG} + V_{UF,extra}$$

over so many treatment sessions BS_d with d=1, d=2, d=3, and so on, until the overhydration $V_{OH}$ at the end of one of the following dialysis sessions is completely depleted, i.e. the patient finally reaches his dry weight $m_{dry}$.

At the end of the transitional regimen (or the transitional phase) (day 27), a new equilibrium, with which the patient reaches his/her dry weight $m_{dry}$ at the end of the future dialysis session without intradialytic diffusive salt supply, is now achieved in the desired treatment regimen (regimen 2), as shown in FIG. 3 in the middle.

Both methods, on the one hand the stepwise reduction of the diffusive salt supply, as exemplarily described in FIG. 2, and on the other hand the initial reduction of the UF volume at the beginning of the transitional phase with subsequent return to the dry weight, as exemplarily described in FIG. 3, may be combined together.

In addition to a linear distribution of reduction of salt supply or return to the dry weight, more complicated algorithms are encompassed. If periodicities are recognized, e.g., when analyzing the diffusive salt intake in the previous treatment regimen, e.g., that the salt intake deviates after the long dialysis interval from the one in the short intervals, then this analysis may be transferred onto the specification of the diffusive salt intake. Likewise, the return to the dry weight may be done in a manner other than linear (rather e.g., exponential) or taking into consideration the presence of a long or short interval. For example, it may be in that a return to dry weight is only effected after the short interval, so that the UF volume, which anyhow has increased after the long interval, is not further increased.

In further modifications of the method, the residence time for a peritoneal dialysis liquid in the abdomen is changed over several treatment sessions. Setting the transitional treatment regimen thus encompasses or is the setting of different residence times of the introduced fluid. The residence time is related to the diffusive sodium balance.

| Table of the used parameters | |
|---|---|
| BS_d | treatment session wherein d = 1, . . . , n with n is the number of the treatment days of the transitional regimen |
| BS_d mit d = 1 | the treatment session upcoming as first |
| $M_{diff,target\_total}$ | total target sodium balance |
| $M_{diff,minus}$ (d) | diffusive sodium balance on day d |

Table of the used parameters

| | |
|---|---|
| $M_{\mathit{diff,target}}$ (d) | target sodium balance (target value for the diffusive intradialytic sodium balance) for the treatment day d |
| $M_{\mathit{diff,tolerated}}$ (d) | value of a sodium balance tolerated by the patient on treatment day d |
| $V_{UF}$ | ultrafiltration volume, UF volume |
| $V_{UF}$ (d) | ultrafiltration volume (UF volume), which should be withdrawn in the treatment session on day d |
| $V_{UF,max}$ | maximal tolerated ultrafiltration volume |
| $V_{UF,minus}$ | correction value (downwards) |
| $V_{UF,extra}$ | correction value (upwards) |
| $V_{IDWG}$ | interdialytic weight or liquid increase |
| $V_{OH}$ | "overhydration" predialytic overhydration |
| $V_{EC}$ | extracellular volume |
| $V_{IC}$ | intracellular volume |
| $m_{dry}$ | dry weight, target dry weight |
| $V_{TBW,dry}$ | total body water volume belonging to the dry weight |
| $V_{TBW}$ | total body water volume |
| $c_j$ | concentration of all ions contributing to the total conductivity |
| $c_{plasma,pre}$ | predialytic plasma sodium concentration |
| $c_{plasma,post}$ | post dialytic plasma sodium concentration |
| $c_{di}$ | medium dialysis sodium; sodium concentration in the dialysis liquid upstream of the dialyzer |
| $c_{do}$ | sodium concentration in the dialysate downstream of the dialyzer |
| $c_{osm,j}$ | osmotic equilibrium |
| $\sigma$ | temperature-compensated total conductivity |
| $\sigma_{Ofs}$ | Offset |
| $\gamma_j$ | (known) specific conductivity |
| $\Psi_j$ | parameter constellation or parameter set |
| $Q_d$ | total flow of fresh dialysis liquid |
| RBV | relative blood volume |
| $\xi$ | intradialytic symptoms |
| d − 1 | the treatment day preceding the treatment day d |
| d | treatment day, day, date |
| d + 1 | treatment day following the treatment day d |
| EC | extracellular compartment, extracellular space |
| IC | intracellular compartment, intracellular space |
| Kt/V | dialysis efficiency measure |

LIST OF REFERENCE NUMERALS 25 addition point for heparin (optional)
29 venous blood chamber (optional)
31 ventilation device
100 blood treatment apparatus
101 blood pump
102 dialysate outlet line, effluent inlet line
104 dialysis liquid inlet line
106 sensor
108 sensor
111 pump for substituate
121 pump for dialysis liquid
131 pump for dialysate or effluent
150 control device or closed-loop control device
200 source containing dialysis liquid
201 source containing substituate, optional
300 extracorporeal blood circuit
301 first line (arterial line section)
302 (first) tube clamp
303 blood filter or dialyzer
303a dialysis liquid chamber
303b blood chamber
303c semi-permeable membrane
305 second line (venous line section)
306 (second) tube clamp
400 effluent bag
600 sink or basin
H1 bag heating with bag (substituate)
H2 bag heating with bag (dialysis liquid)
PS1, PS2 arterial pressure sensor (optional)
PS3 pressure sensor (optional)
PS4 pressure sensor for measuring the filter pressure

The invention claimed is:

1. A method for altering treatment parameters of a treatment apparatus used for dialyzing a patient over a plurality of treatment sessions, the method comprising:
   determining a diffusive total target sodium balance;
   determining a transitional treatment regimen by which the diffusive total target sodium balance is achieved over the plurality of treatment sessions, wherein determining the transitional treatment regimen comprises:
   specifying, prior to starting a first treatment session, a first corrected volume by mathematically adjusting the value of a first initial ultrafiltration volume in order to achieve a target dry weight or another weight target value;
   controlling, based on the determined transitional treatment regimen and while dialyzing the patient, the following:
   an ultrafiltration pump of the treatment apparatus; and
   a concentration of sodium chloride in a dialysis liquid used by the treatment apparatus;
   and adjusting a second initial ultrafiltration volume to be withdrawn during a second treatment session of the plurality of treatment sessions to a second corrected volume of the second treatment session in order to achieve a second ultrafiltration volume of the second treatment session, wherein:
   the second corrected volume of the second treatment session of the plurality of treatment sessions is less than the first corrected volume of the first treatment session.

2. The method according to claim 1, wherein the diffusive total target sodium balance is between −300 mmol and +300 mmol.

3. The method according to claim 1, wherein the diffusive total target sodium balance is 0 mmol.

4. The method according to claim 1, wherein a respective initial ultrafiltration volume to be withdrawn during a respective treatment session is adjusted to a respective corrected volume for each of the plurality of treatment sessions following the first treatment session until a sum of each corrected volume of each treatment session of the plurality of treatment sessions reaches a total volume that assumes or exceeds a first ultrafiltration volume of the first treatment session.

5. The method according to claim 4, wherein the respective initial ultrafiltration volume to be withdrawn during the respective treatment session is adjusted to the respective corrected volume for a plurality of successive treatment sessions.

6. The method according to claim 1, wherein the step of determining the transitional treatment regimen comprises:
   determining a diffusive target sodium balance ($M_{\mathit{diff,target}}$ (d); for an upcoming treatment session:

$$M_{\mathit{diff,target}}(d) = M_{\mathit{diff,tolerated}}(d-1) - M_{\mathit{diff,minus}}(d),$$

wherein the following applies:
   $M_{\mathit{diff,target}}$(d) is a value of a diffusive sodium balance desired during the upcoming treatment session;
   $M_{\mathit{diff,tolerated}}$(d−1) is a value of a diffusive sodium balance tolerated by the patient during the upcoming treatment session; and
   $M_{\mathit{diff,minus}}$(d) is a determined value of a diffusive sodium balance by which $M_{\mathit{diff,tolerated}}$(d−1) is mathematically reduced.

7. The method according to claim 6, wherein the following applies:

$$M_{diff,tolerated}(d-1) M_{diff,target}(d-1)$$

wherein the following applies:
$M_{diff,target}(d-1)$ is the value of the desired, achieved, or adjusted diffusive sodium balance for a treatment session preceding the upcoming treatment session.

8. The method according to claim 6, wherein the steps of claim 6 are repeated for successive treatment sessions of the plurality of treatment sessions until the value of the diffusive sodium balance desired during the upcoming treatment session assumes, or is less than, the diffusive total target sodium balance.

9. The method according to claim 1, wherein the step of determining the transitional treatment regimen comprises:
determining that the diffusive total target sodium balance is to be between −300 mmol and +300 mmol.

10. The method according to claim 1, wherein the step of determining the transitional treatment regimen comprises:
determining that the diffusive total target sodium balance is 0 mmol.

11. A control device or a closed-loop control device configured for performing a method comprising:
determining a diffusive total target sodium balance;
determining a transitional treatment regimen by which the diffusive total target sodium balance is achieved over a plurality of treatment sessions, wherein determining the transitional treatment regimen comprises:
specifying, prior to starting a first treatment session, a first corrected volume by mathematically adjusting the value of a first initial ultrafiltration volume in order to achieve a target dry weight or another weight target value;
controlling, based on the determined transitional treatment regimen and while dialyzing a patient using a treatment apparatus, the following:
an ultrafiltration pump of the treatment apparatus; and
a concentration of sodium chloride in a dialysis liquid used by the treatment apparatus; and
adjusting a second initial ultrafiltration volume to be withdrawn during a second treatment session of the plurality of treatment sessions to a second corrected volume of the second treatment session in order to achieve a second ultrafiltration volume of the second treatment session, wherein:
the second corrected volume of the second treatment session of the plurality of treatment sessions is less than the first corrected volume of the first treatment session.

12. A blood treatment apparatus comprising:
a control device configured to control the blood treatment apparatus by executing a method, the method comprising:
determining a diffusive total target sodium balance;
determining a transitional treatment regimen by which the diffusive total target sodium balance is achieved over a plurality of treatment sessions, wherein determining the transitional treatment regimen comprises:
specifying, prior to starting a first treatment session, a first corrected volume by mathematically adjusting the value of a first initial ultrafiltration volume in order to achieve a target dry weight or another weight target value;
controlling, based on the determined transitional treatment regimen and while dialyzing a patient, the following:
an ultrafiltration pump of the blood treatment apparatus; and
a concentration of sodium chloride in a dialysis liquid used by the blood treatment apparatus; and
adjusting a second initial ultrafiltration volume to be withdrawn during a second treatment session of the plurality of treatment sessions to a second corrected volume of the second treatment session in order to achieve a second ultrafiltration volume of the second treatment session, wherein:
the second corrected volume of the second treatment session of the plurality of treatment sessions is less than the first corrected volume of the first treatment session.

13. The blood treatment apparatus according to claim 12, wherein the blood treatment apparatus is an apparatus for chronic renal replacement therapy or for continuous renal replacement therapy.

14. The blood treatment apparatus according to claim 12, wherein the blood treatment apparatus is a peritoneal dialysis apparatus, hemodialysis apparatus, hemofiltration apparatus, or hemodiafiltration apparatus.

15. The blood treatment apparatus according to claim 12, further comprising sensors arranged upstream and downstream of a dialyzer of the blood treatment apparatus for measuring the at least one of:
an electrolyte balance, and a liquid balance.

16. The blood treatment apparatus according to claim 12, further comprising sensors arranged upstream or downstream of a dialyzer of the blood treatment apparatus for measuring the at least one of:
an electrolyte balance, and a liquid balance.

* * * * *

UNITED STATES PATENT AND TRADEMARK OFFICE
CERTIFICATE OF CORRECTION

PATENT NO. : 12,324,875 B2
APPLICATION NO. : 18/462881
DATED : June 10, 2025
INVENTOR(S) : Andreas Maierhofer Page 1 of 1

It is certified that error appears in the above-identified patent and that said Letters Patent is hereby corrected as shown below:

In the Claims

Claim 6
Column 22, Lines 55-56, delete "($M_{diff,target}(d)$;" and insert -- ($M_{diff,target}(d)$)) --.

Claim 7
Column 23, Line 4, delete "$M_{diff,tolerated}(d-1)M_{diff,target}(d-1)$" and insert
-- $M_{diff,tolerated}(d-1)=M_{diff,target}(d-1)$ --.

Claim 9
Column 23, Line 18, delete "between-300" and insert -- between -300 --.

Signed and Sealed this
Twenty-sixth Day of August, 2025

Coke Morgan Stewart
*Acting Director of the United States Patent and Trademark Office*